United States Patent [19]
Geiser et al.

[11] Patent Number: 6,106,470
[45] Date of Patent: Aug. 22, 2000

[54] METHOD AND APPARTUS FOR CALCULATING DISTANCE BETWEEN ULTRASOUND IMAGES USING SUM OF ABSOLUTE DIFFERENCES

[75] Inventors: Brian Peter Geiser, Hartland, Wis.; William Thomas Hatfield, Schenectady, N.Y.; Vaishali Vilas Kamat, Waukesha, Wis.; Steven Charles Miller, Pewaukee, Wis.; Larry Y. L. Mo, Waukesha, Wis.; Todd Michael Tillman, West Milwaukee, Wis.; Boris Yamrom, Schenectady, N.Y.

[73] Assignee: General Electric Company, Schenectady, N.Y.

[21] Appl. No.: 09/299,032

[22] Filed: Apr. 23, 1999

Related U.S. Application Data

[63] Continuation-in-part of application No. 09/045,780, Mar. 20, 1998, abandoned.

[51] Int. Cl.$^7$ ........................................................ A61B 8/00
[52] U.S. Cl. ............................................ 600/443; 128/916
[58] Field of Search ..................................... 600/443, 447, 600/437, 441; 128/916; 73/626

[56] References Cited

U.S. PATENT DOCUMENTS

| | | | |
|---|---|---|---|
| 5,226,113 | 7/1993 | Cline et al. | 395/124 |
| 5,485,842 | 1/1996 | Quistgaard | 128/660.07 |
| 5,582,173 | 12/1996 | Li | 128/660.07 |
| 5,655,535 | 8/1997 | Friemel et al. | 128/660.07 |
| 5,782,766 | 7/1998 | Weng et al. | 600/443 |
| 5,876,342 | 3/1999 | Chen et al. | 600/443 |
| 5,899,861 | 5/1999 | Friemel et al. | 600/443 |

FOREIGN PATENT DOCUMENTS

97/00482  1/1997  WIPO .

OTHER PUBLICATIONS

Bohs et al., "A Novel Method for Angle Independent Ultrasonic Imaging of Blood Flow and Tissue Motion, " IEEE Trans. Biomed. Engng., vol. 38, No. 3, pp. 280–286 (Mar. 1991).

Chen et al., "Determination of Scan–Plane Motion Using Speckle Decorrelation: Theoretical Considerations and Initial Test, " Int. J. Imaging Syst. Technol., vol.8, pp. 38–44 (1997).

Trahey et al., "Angle Independent Ultrasonic Detection of Blood Flow, " IDDD Trans. Biomed. Engng., vol. 34, No. 12, pp. 965–967 (Dec. 1987).

Shehada et al., "Ultrasound Methods for Investigating the Non–Newtonian Characteristics of Whole Blood, " IEEE Trans. Ultrasonics, Ferroelec. & Freq. Control, vol. 41, No. 1, pp. 96–104 (Jan. 1994).

*Primary Examiner*—Marvin M. Lateef
*Assistant Examiner*—Ali M. Imam
*Attorney, Agent, or Firm*—Marvin Snyder; Douglas E. Stoner

[57] ABSTRACT

A method and apparatus for calculating the inter-slice spacing in a data volume and registering the slices of that volume using SAD calculations. The resulting transformed data volume is then three-dimensionally reconstructed using a projection technique. If during scanning the probe is translated in the Z direction and at the same time is shifted in the X and/or Y direction, the SAD value will be artificially high. By translating two adjacent images with respect to each other in the X direction and then in the Y direction, and searching for the minimum SAD value, the amount of shift in the X and/or Y direction can be determined and that shift can then be removed. Also by rotating two slices with respect to each other and looking for a minimum SAD value, rotational motion of the probe during scanning can be removed.

30 Claims, 11 Drawing Sheets

# METHOD AND APPARTUS FOR CALCULATING DISTANCE BETWEEN ULTRASOUND IMAGES USING SUM OF ABSOLUTE DIFFERENCES

RELATED PATENT APPLICATION

This is a Continuation-in-Part of U.S. patent application Ser. No. 09/045,780 filed on Mar. 20, 1998, now abandoned.

FIELD OF THE INVENTION

This invention generally relates to three-dimensional ultrasound imaging of the human anatomy for the purpose of medical diagnosis. In particular, the invention relates to methods and apparatus for three-dimensional imaging of the human anatomy by detecting the ultrasonic echoes reflected from a scanned volume in a human body.

BACKGROUND OF THE INVENTION

Conventional ultrasound scanners create two-dimensional B-mode images of tissue in which the brightness of a pixel is based on the intensity of the echo return. Alternatively, in a color flow imaging mode, the movement of fluid (e.g., blood) or tissue can be imaged. Measurement of blood flow in the heart and vessels using the Doppler effect is well known. The phase shift of backscattered ultrasound waves may be used to measure the velocity of the backscatterers from tissue or blood. The Doppler shift may be displayed using different colors to represent speed and direction of flow. In power Doppler imaging, the power contained in the returned Doppler signal is displayed. Although the following disclosure refers predominantly to B-mode imaging for the sake of brevity, the present invention applies to any mode of ultrasound imaging.

Two-dimensional ultrasound images are often hard to interpret due to the inability of the observer to visualize the two-dimensional representation of the anatomy being scanned. In addition, it may not be possible to acquire the precise view needed to make a diagnosis due to probe geometry or poor access to the area of interest. However, if the ultrasound probe is swept over an area of interest and two-dimensional images are accumulated to form a three-dimensional data volume, the anatomy becomes much easier to visualize for both the trained and untrained observer. Also views which cannot be acquired due to probe geometry or poor access to the area of interest can be reconstructed from the three-dimensional data volume by constructing slices through the volume at the difficult to obtain angle.

In order to generate three-dimensional images, the imaging system computer can transform a source data volume retrieved from memory into an imaging plane data set. The successive transformations may involve a variety of projection techniques such as maximum, minimum, composite, surface or averaged projections made at angular increments, e.g., at 10° intervals, within a range of angles, e.g., +90° to −90°. Each pixel in the projected image includes the transformed data derived by projection onto a given image plane.

In free-hand three-dimensional ultrasound scans, a transducer array (1D to 1.5D) is translated in the elevation direction to acquire a set of image planes through the anatomy of interest. These images can be stored in memory and later retrieved by the system computer for three-dimensional reconstruction. If the spacings between image frames (hereinafter "inter-slice spacings") are known, then the three-dimensional volume can be reconstructed with the correct aspect ratio between the out-of-plane and scan plane dimensions. If, however, the estimates of the inter-slice spacing are poor, significant geometric distortion of the three-dimensional object can result.

In the prior art, a variety of motion control and position-sensing methods have been proposed to control or track the elevational motion of the ultrasound probe respectively. However, these systems are often costly and cumbersome to use in a clinical environment. Therefore, to reconstruct a three-dimensional image with good resolution in the elevation direction, it is highly desirable to be able to estimate the scan plane displacements directly from the degree of speckle decorrelation between successive slices.

If the ultrasound probe is swept over an area of body and the slices of pixel data are stored in memory, a three-dimensional data volume can be acquired. The data volume can be used to form a three-dimensional view of the area of interest. The registration of these slices of pixel data is critical to the quality of the three-dimensional reconstruction. Since ultrasound probes are commonly held in the sonographer's hand and moved over the body in the course of an ultrasound examination, it would be desirable for the sonographer to acquire the three-dimensional data volume with a manual sweep. However, this makes the individual slices difficult to register.

A method and an apparatus, disclosed in U.S. patent application Ser. No. 09/045,780, for tracking scan plane motion in free-hand three-dimensional ultrasound scanning uses adaptive speckle correlation. The method employs a correlation index which adapts to different display dynamic range and post-processing filters. In particular, this method is based on computing the sum of absolute differences (SAD) between corresponding pixels in two kernels being correlated. The preferred method comprises the steps of choosing a kernel within each image frame for correlation calculations; rejecting duplicate image frames; measuring the degree of correlation between successive image frames; rejecting correlation estimates which may be associated with hand jitter and other artifacts; and computing the average frame-to-frame (i.e., inter-slice) spacing based on the average correlation estimate. These steps are performed by a host computer which interfaces with the cine memory. A major benefit of this image-based motion tracking technique is that it enables three-dimensional reconstruction with good geometric fidelity, without use of any external position-sensing device.

The foregoing method works well when the probe is moved in a linear fashion. However, if the probe is shifted in the X or Y plane or rotated about the X, Y or Z axis while being translated in the Z direction, a large error in the inter-slice distance estimate can be introduced. Thus, there is a need for a method which takes these shifts and rotations into account when estimating the inter-slice distance.

SUMMARY OF THE INVENTION

The invention is a method and apparatus for calculating the inter-slice spacing in a data volume and registering the slices of that volume using SAD calculations. Preferably these operations are performed after duplicate frames have been removed using the same SAD technique.

If the probe is translated in the Z direction and at the same time is shifted in the X and/or Y direction, the SAD value will be artificially high.

By iteratively translating two adjacent images with respect to each other in the X direction and then in the Y direction, and searching for the minimum SAD value, the amount of shift in the X and/or Y direction can be determined and that shift can then be removed.

Also by iteratively rotating two slices with respect to each other and looking for a minimum SAD value, rotational motion can be removed.

In accordance with the one preferred embodiment of the invention, the SAD technique is used to correct for shifts in the X and Y directions and for rotation about the Z axis, and then calculate the inter-slice spacing. The X and Y shifts and rotation about the Z axis from slice to slice are estimated by comparing a single sub-region (i.e., kernel) of each pair of adjacent slices. These values are used to register each slice with its preceding slice. The transformed data volume then undergoes three-dimensional reconstruction.

In accordance with another preferred embodiment, the SAD technique is used in multiple sub-regions (e.g., three) to estimate the X and Y shifts of each slice relative to its preceding slice in each sub-region. The inter-slice spacing for each sub-region is then calculated using the SAD. The resulting points determine the plane of slice i. Based on the equation for this plane, the host computer calculates the pixel coordinates of the plane midpoint and the inter-slice spacing separating that midpoint from the midpoint of plane (i−1). The host computer then performs a series of calculations to arrive at a cumulative transformation which transforms plane 0 into plane i. The pixel values of plane i are then inserted into the location in the data volume determined by transforming the pixel coordinates in plane i with the cumulative transformation. This algorithm is repeated until all slices have been processed and a transformed data volume with registered slices is obtained.

DETAILED DESCRIPTION OF THE PREFERRED EMBODIMENTS

Figure 1:
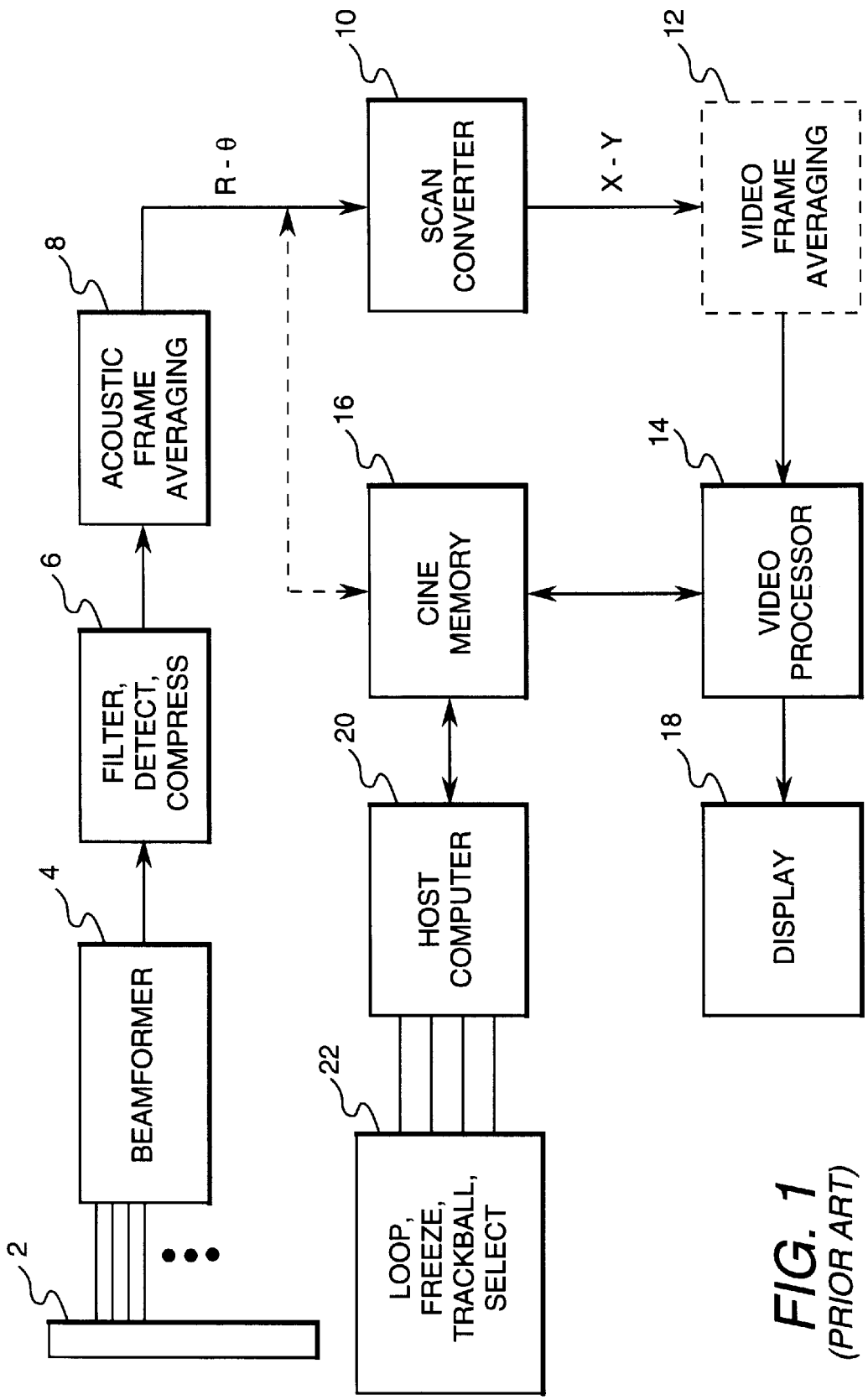
FIG. 1 is a block diagram generally depicting various subsystems of a conventional real-time digital ultrasound imaging system.

The basic signal processing chain in a B-mode imaging system is depicted in FIG. 1. An ultrasound transducer array 2 is activated to transmit an ultrasound beam focused at a transmit focal position. The return RF signals are detected by the transducer elements and then dynamically focused at successive ranges along a scan line by the beamformer 4 to form a receive vector. The beamformer output data (I/Q or RF) for each scan line is passed through a B-mode processing chain 6 which includes equalization filtering, envelope detection and logarithmic compression. Depending on the scan geometry, up to a few hundred vectors may be used to form a single acoustic image frame. To smooth the temporal transition from one acoustic frame to the next, some acoustic frame averaging 8 may be performed before scan conversion. For a sector scan, compressed images in R-θ format are converted by the scan converter 10 into X-Y format for display. On some systems, frame averaging may be performed on the X-Y data (indicated by dashed block 12) rather than the acoustic frames before scan conversion, and sometimes duplicate video frames may be inserted between acoustic frames in order to achieve a given video display frame rate. The scan-converted frames are passed to a video processor 14, which basically maps the scan-converted data to a display gray or color map for video display.

System control is centered in a host computer 20, which accepts operator inputs through an operator interface 22 and in turn controls the various subsystems. (In FIG. 1, the system control lines from the host computer to the various subsystems have been omitted for the sake of simplicity.) During imaging, a long sequence of the most recent images are stored and continuously updated automatically in a cine memory 16. Some systems are designed to save the R-θ acoustic images (this data path is indicated by the dashed line in FIG. 1), while other systems store the X-Y video images. The image loop stored in cine memory 16 can be reviewed on the display monitor via trackball control (interface 22), and a section of the image loop can be selected for hard disk storage.

For an ultrasound scanner with free-hand three-dimensional imaging capability, the selected image sequence stored in cine memory 16 is transferred to the host computer 20 for three-dimensional reconstruction. The result is written back into another portion of the cine memory or to scan converter memory, from where it is sent to the display system 18 via the video processor 14.

Figure 2:
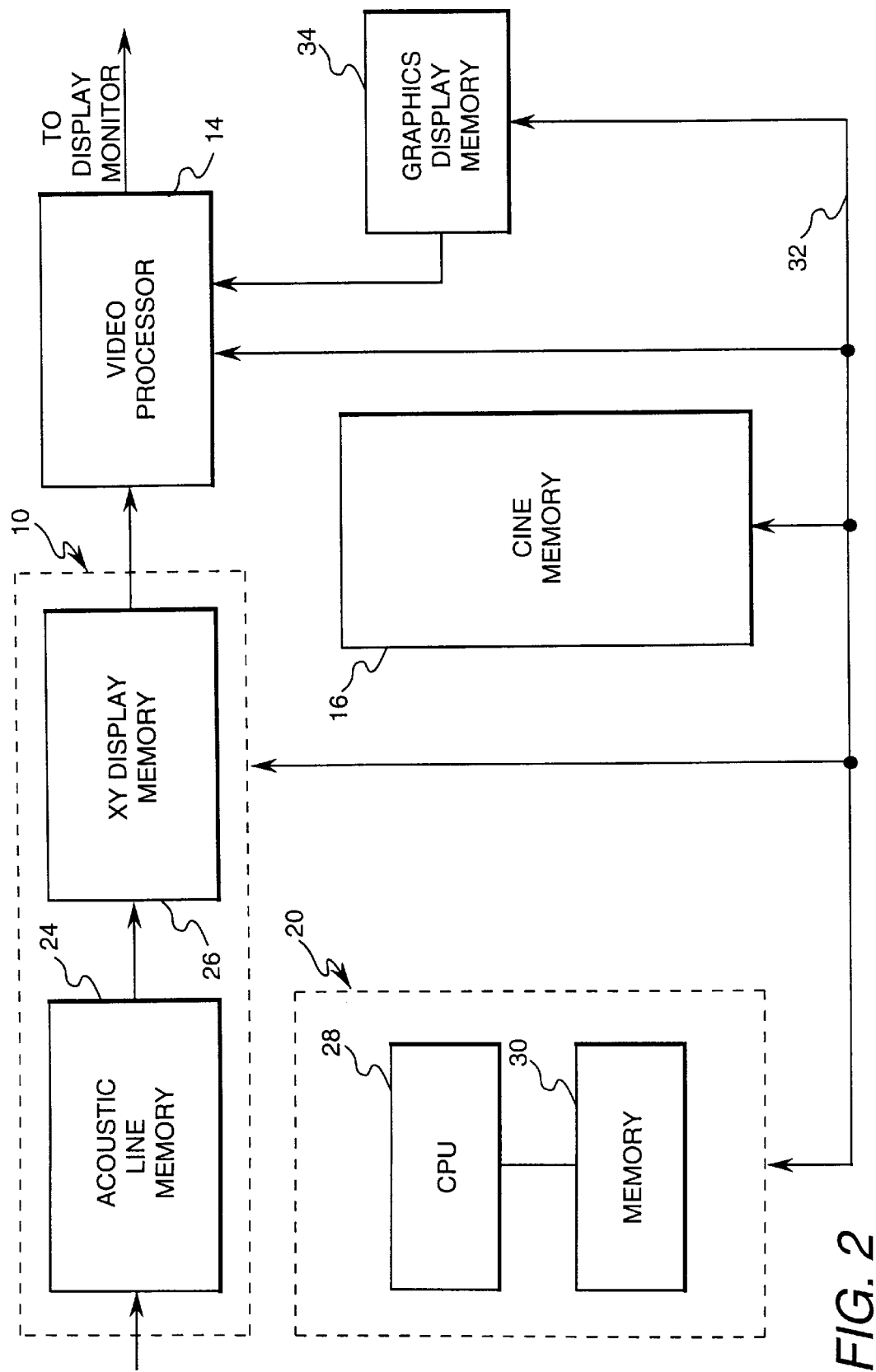
FIG. 2 is a block diagram showing the means for reconstructing frames comprising successive projections of pixel data in accordance with the preferred embodiment of the present invention.

Referring to FIG. 2, the scan converter 10 comprises an acoustic line memory 24 and an XY display memory 26. The B-mode imaging data stored in polar coordinate (R-θ) sector format in acoustic line memory 24 is transformed to appropriately scaled Cartesian coordinate intensity data, which is stored in XY display memory 26. Each image frame out of XY display memory 26 is sent to the video processor 14. Before gray mapping, frames of B-mode imaging data in the video processor 14 are stored in cine memory 16 on a first-in, first-out basis. Storage can be continuous or as a result of an external trigger event. The cine memory 16 is like a circular image buffer that runs in the background, capturing image data that is displayed in real time to the user. When the user freezes the system (by operation of an appropriate device on the operator interface 22), the user has the capability to view image data previously captured in cine memory.

In accordance with the preferred embodiment of the invention, the selected image sequence stored in cine memory 16 is transferred to the host computer 20 for three-dimensional reconstruction. The multiple frames of imaging data acquired during the sweep of the probe form a three-dimensional data volume. The host computer 20 retrieves the region of interest from cine memory 16 and reconstructs projected images onto various imaging planes. The data resulting from each projection is written back into another portion of the cine memory or to scan converter memory, from where it is sent to the display monitor 18 via the video processor 14.

The host computer 20 comprises a central processing unit (CPU) 28 and system memory 30. The CPU 28 is programmed to transform an acquired volume of imaging data into a multiplicity of three-dimensional projection images taken at different angles. The CPU 28 controls the flow of data between XY display memory 26, video processor 14, cine memory 16 and the CPU itself via the system control bus 32. Each frame of imaging data, representing one of a multiplicity of scans or slices through the object being examined, is stored sequentially in the acoustic line memory 24, in the XY memory 26 and in the video processor 14. Before gray mapping, frames of B-mode imaging data are sent from the video processor to the cine memory 16. A stack of frames, representing the scanned object volume, is stored in cine memory 16, forming a source data volume. Once the source data volume has been acquired, the CPU 28 can provide three-dimensional projections of the data as well as arbitrary slices through the source data volume.

The conventional system has the capability to superimpose graphical symbols on any ultrasound image. The superimposition of graphics on the image frame is accomplished in the video processor 14, which receives the ultrasound image frame from the XY display memory 26 and the graphics data from a graphics display memory 34. The graphics data is processed and input into the graphics display memory 34 by the host computer 20 or by a dedicated graphics processor (not shown)

In order to generate three-dimensional images, the CPU 28 can transform a source data volume retrieved from cine memory 16 into an imaging plane data set. Each pixel in the projected image includes the transformed data derived by projection onto a given image plane.

Figure 3:
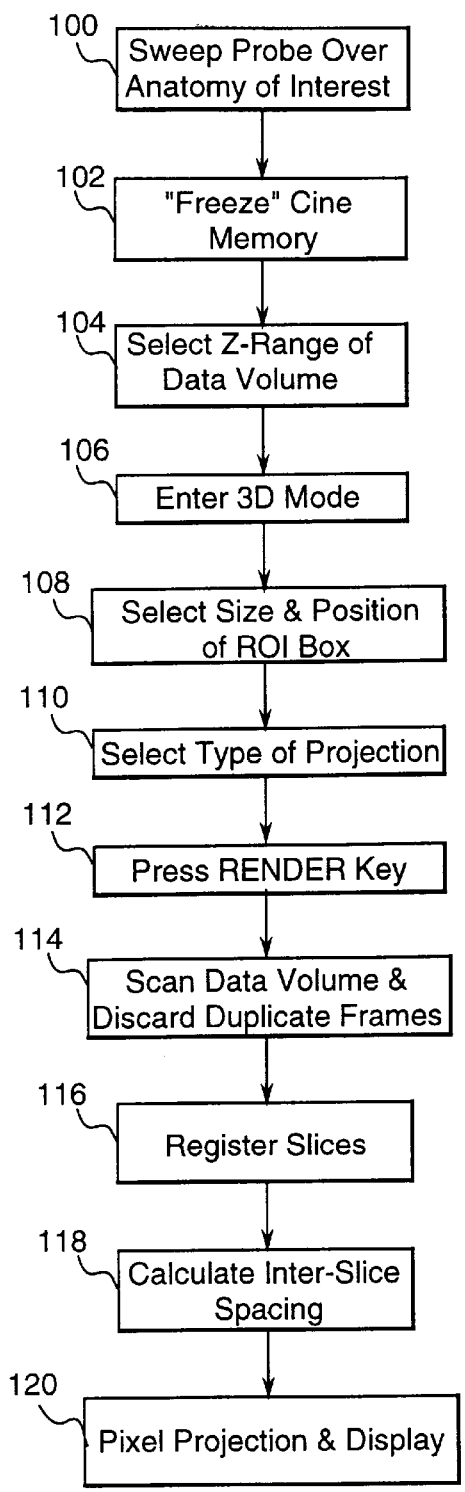
FIG. 3 is a flowchart showing a procedure for acquiring and displaying three-dimensional imaging data.

FIG. 3 is a flowchart showing an image acquisition and display procedure which employs any one of a plurality of selectable projection techniques. The user begins by sweeping the ultrasound probe over an area of interest (step 100). For example, the sweep may be acquired by a free-hand sweep in a linear or rocking motion. Once the data is acquired, the user "freezes" the cine memory (step 102) by depressing the Freeze key and then selects the range of cine memory frames (slices) to be included in the Z-dimension of the data volume (step 104). The operator accomplishes the latter step by moving a trackball. A Z-dimension select gauge appears on the display screen when the trackball is moved. The trackball is then used to control the position of an indicator relative to the gauge. The indicator can be moved to a desired left end point and then the left end point is locked by depression of predetermined key on the operator interface. Then the indicator can be moved to a desired right end point and then the right end point is locked by depression of the same predetermined key. This establishes the slices to be included in the data volume. The operator then enters the "3D mode" by depressing the appropriate key on the interface (step 106).

Upon entering the 3D mode, the operator must first select the X and Y dimensions and location of the ROI within the data volume (step 108). This step is accomplished by manipulating a region of interest box which appears in a default position on the display screen in response to depression of the 3-D mode key. The region of interest box can be sized and translated in X and Y to encompass an imaged structure which appears on a sector scan image. The region of interest box is translated by moving the trackball and is sized by operation of a four-sided rocker switch incorporated in the operator interface.

After the ROI has been defined, the operator selects (step 110 in FIG. 3) the type of three-dimensional projection (minimum, maximum or average pixel projection, surface, composite, etc.) and the display mode desired, and then presses a render key (step 112). The defined ROI is then retrieved from cine memory 16 (see FIG. 2) by the host computer 20. The host computer scans the retrieved data for duplicate frames and discards them (step 114). In accordance with one preferred embodiment of the invention, the host computer then registers the slices (step 116) and calculates the inter-slice spacing for the data set (step 118). (The inter-slice spacing is assumed to be constant over the length of the data volume.) After calculation of the inter-slice spacing, the host computer performs the selected pixel projection of the defined data volume based on the calculated inter-slice spacing (step 118). The projected three-dimensional image is sent to the cine memory 16 and then on to the video processor 14. The video processor 14 causes the projected three-dimensional image to be displayed on the display screen. The data slices are acquired along the Z axis.

Figure 4:
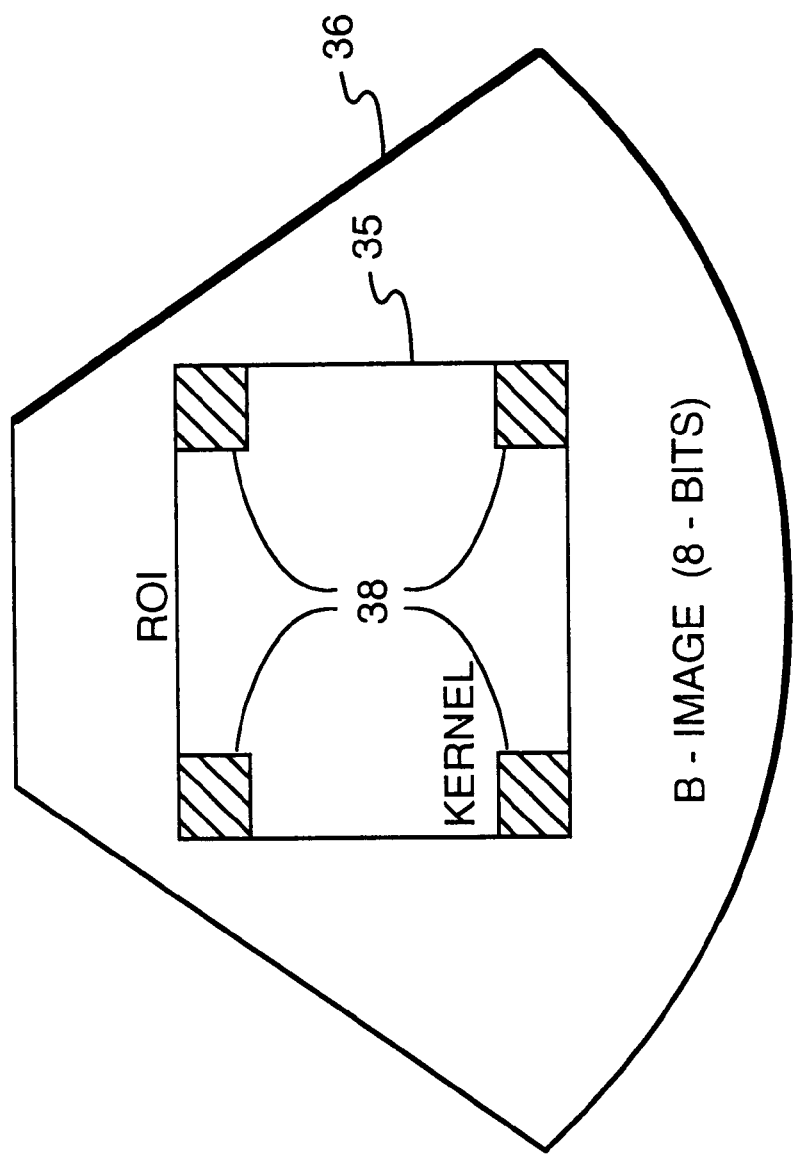
FIG. 4 is a schematic showing a typical region-of-interest box within one image frame and further showing a selected kernel within the region of interest.

One method for calculating the inter-slice distance is taught in U.S. patent application Ser. No. 09/045,780. FIG. 4 shows a typical ROI box 35 within one image frame 36 (a sector scan in this example) as selected by the user. It will be assumed that N frames (numbered from i=0 to (N−1)) generated by a free-hand scan are stored in cine memory.

One way of estimating the average inter-slice spacing d for three-dimensional reconstruction (which is performed by the host computer based on the data retrieved from cine memory) will be described with reference to FIGS. 4 and 5. First, a kernel 38 (M×M pixels in this example, but in general the kernel does not have to be square) within the ROI 35 that shows a relatively pure speckle pattern (no macroscopic structures) must be identified (step 40) since the correlation method is based on the statistics of pure speckle arising from a diffuse scattering medium. The kernel 38 can be selected manually (e.g., by means of a trackball) based on visual judgment of one or more image frames. Alternatively, some automated method can be used to search for a kernel whose pixel amplitude histogram is consistent with the theoretical speckle distribution. For example, such tests can be based on a measure of the histogram width relative to normal dynamic range settings. Kernels whose mean pixel values are too low (no signal) or whose variances are too large (not homogeneous) should be rejected. As shown in FIG. 4, a good initial kernel 38 to test is one at any of the four corners of the ROI 35—assuming the user tends to position the structures of interest in the center of the ROI.

Figure 5:
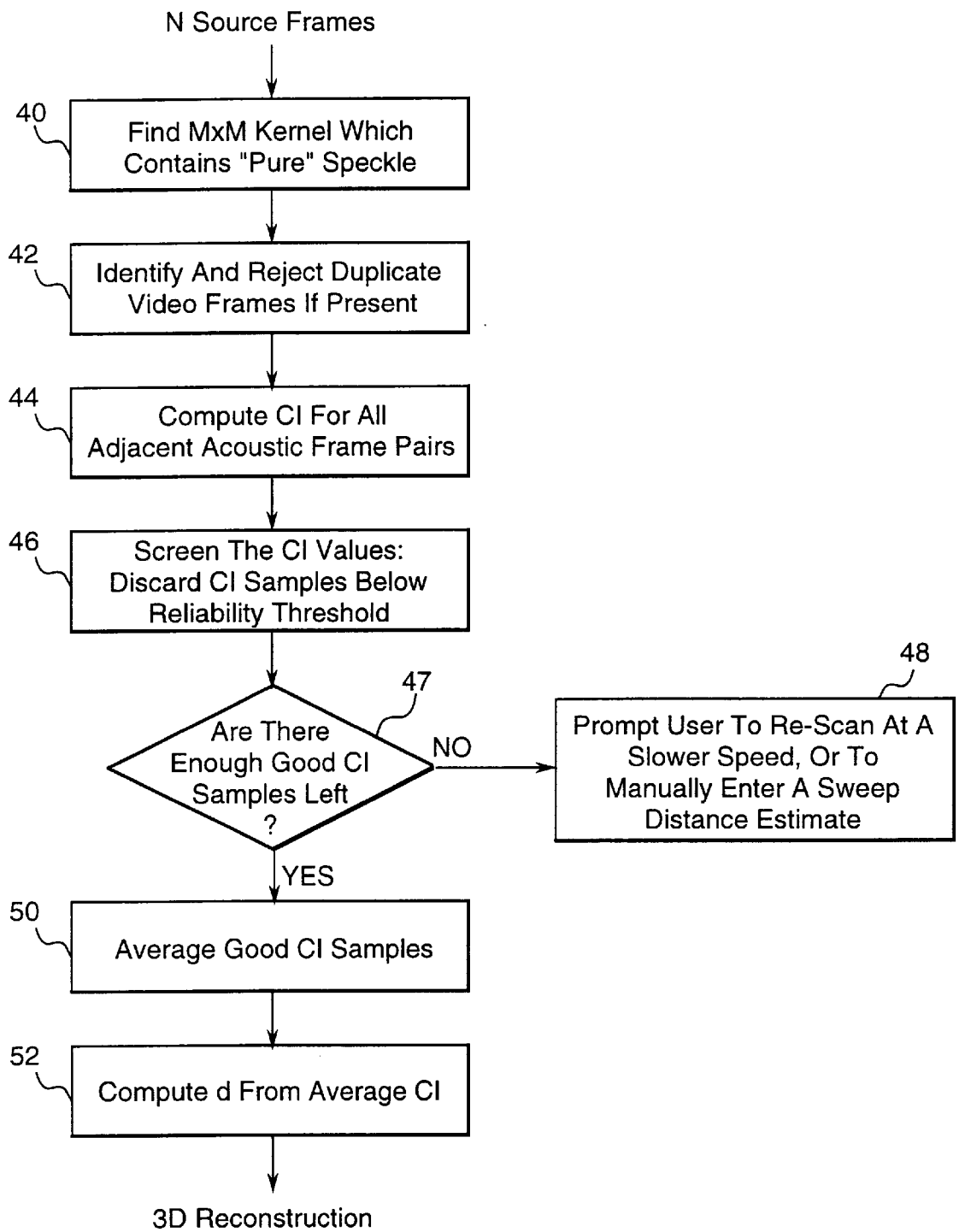
FIG. 5 is a flowchart showing the steps of a method by which the average frame-to-frame spacing d can be estimated for use in three-dimensional reconstruction.

Before proceeding to compute the correlation between kernels in successive image frames, any duplicate image frames present in the N source frames are identified and rejected (step 42 in FIG. 5). In step 44, a correlation index (CI) is computed for all adjacent frame pairs in the remaining set of acoustic frames. A correlation index is used which can be considered as a normalized SAD that can adapt to different kernel sizes, display dynamic ranges and post-processing filters. The correlation index ranges from 100% for identical kernels to zero for completely independent speckle patterns. In principle, the correlation index may also become negative if the two kernels pick up different structures.

In general, there is no guarantee that the kernel chosen based on one frame will also contain a homogeneous speckle pattern in other frames. Hence, a screening test (step 46 in FIG. 5) of the correlation index estimates is in order. For example, one may choose to discard all correlation index samples below a certain reliability threshold (e.g., 20%) that are indicative of axial and/or lateral scan-plane jitter, a skid in the elevation motion, or frame averaging (which can make uncorrelated frames look weakly correlated). It may also be useful to count the remaining good correlation index values (step 47 in FIG. 5) to see if they constitute a significant fraction of the N frames (e.g., "at least 10% of the correlation index values must be good"). If too few frames are reliable (CI>20%), then the user should be prompted (step 48) to either re-scan at a slower and more steady speed, or to manually enter an estimate of the total sweep distance.

If there are enough good correlation index samples, their average should be taken (step 50 in FIG. 5) to reduce statistical variability. The result can be used to compute the corresponding average inter-slice spacing d (step 52), based on a pre-calibrated CI versus d model (stored in memory in the CPU 28 shown in FIG. 2) for each probe type and kernel depth. If there are enough good correlation index samples, the corresponding average d should be quite reliable for three-dimensional reconstruction.

An adaptive method is used to normalize the SAD of two image kernels such that the resultant correlation index is independent of display dynamic range, post-processing filter and kernel size to within reasonable limits. The key idea is to determine from theoretical speckle statistics what the average SAD per pixel would approach if the image kernels were so far apart that they become statistically independent (if there is no frame averaging).

It is well known that the detected speckle amplitude for a diffuse homogeneous scattering medium is described by a Rayleigh distribution. Suppose the image compression prior to display can be modeled by a simple logarithmic function as follows:

$$y = 10 \log [x+1] \qquad (1)$$

Standard statistical operations indicate that if x is Rayleigh distributed, then the probability density function (pdf) of y is $$f_y(y) = \tfrac{2}{m} \exp(ay) \exp(-\tfrac{1}{m}[\exp(ay)-1]) \qquad (2)$$

where $a=(0.1)\ln(10)$ is a constant, and $m=E[x]$ is the expected value of x which is dependent on system gain. For an 8-bit linear gray map, y is mapped to [0, 255] for display and a sample histogram for m=100 is plotted in FIG. 6.

Figure 7:
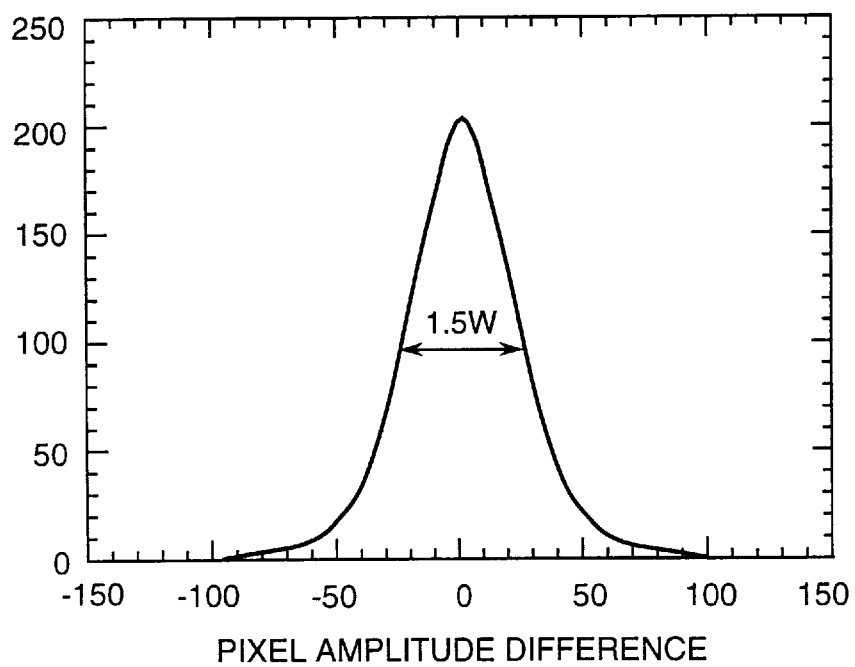
FIG. 7 is a graph showing the probability density distribution $f_y(SAD=|y_1-y_2|)$, where $y_1$ and $y_2$ are independent identically distributed random variables that represent the amplitude of corresponding pixels in two kernels being correlated.

Suppose $y_1$ and $y_2$ are independent identically distributed random variables that represent the amplitude of corresponding pixels in the two kernels being correlated. One needs to determine the pdf of $SAD=|y_1-y_2|$. First, the pdf of $(-y_2)$ is simply the mirror image of that of $y_2$, which is assumed to be the same as that of $y_1$. The pdf of $y_1+(-y_2)$ is given by the convolution of their respective pdfs, which is shown in FIG. 7. Since the pdf of the sum is a symmetric function about zero, the pdf of its absolute value (SAD) is simply the positive half of the distribution (times two).

Figure 6:
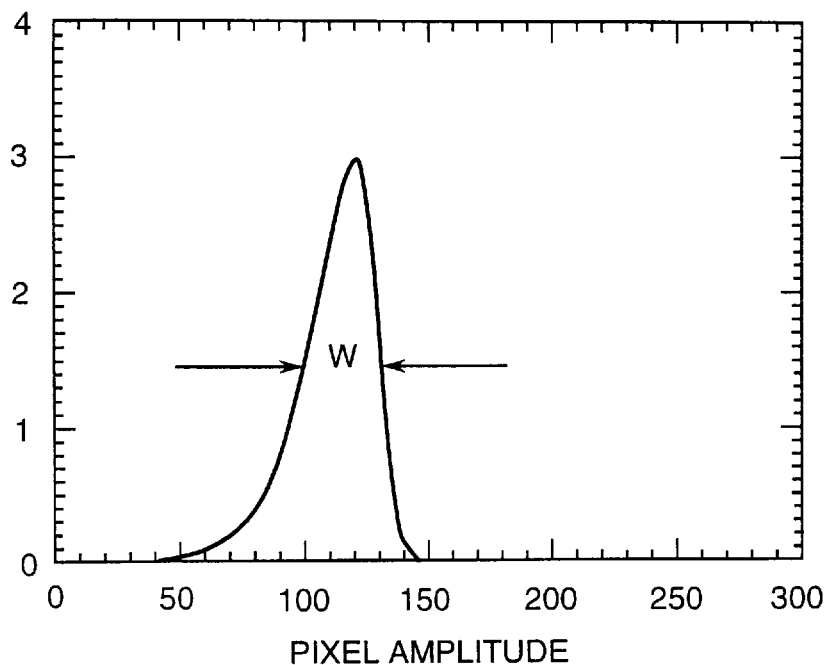
FIG. 6 is a graph showing the probability density distribution $f_y(y)$ of the log-compressed noise spectral power y for m=100, where m=E[x] is the expected value of x.

Note that the half-maximum width w of the pdf of $(y_1-y_2)$ (FIG. 7) is about 1.5 times that of an individual y (FIG. 6). In practice, the compression function may be different from Eq. (1), but one can always follow the same approach to derive the pdf of SAD. If the compression function does not deviate greatly from Eq. (1) and the post-processing spatial filtering effects are mild, the width of the SAD histogram can be approximated by a constant $\gamma$ times that of each image kernel, where $\gamma \cong 1.5$. If the spatial filters are very strong, then the value of $\gamma$ may have to be adjusted accordingly. To those skilled in the art it is clear that the width of the pixel amplitude distribution over an (M×M) pixel kernel in the k-th image frame can also be defined by its rms pixel value, or in accordance with the preferred embodiment, by simply the average absolute deviation as follows:

$$s_k = \frac{1}{M^2} \sum |y_k(i) - mean_k| \qquad (3)$$

in which $y_k(i)$ is amplitude of the i-th pixel, and $mean_k$ is the mean amplitude over all $M^2$ pixels. In general, $s_k$ is a function of dynamic range setting and post-processing spatial filters. Suppose the $SAD_k$ image has been computed for two corresponding kernels in the k-th and (k+1)-th frames as follows:

$$SAD_k = \sum_i |y_{k+1}(i) - y_k(i)| \qquad (4)$$

As the frame separation increases, the average absolute difference per pixel, i.e., $SAD_k/M^2$, will increase from zero to a limiting value of $(\gamma s_k)$ as the two kernels become statistically independent. Hence, a suitable correlation index can be defined as follows:

$$CI_k = \frac{\gamma s_k - |SAD_k|/M^2}{\gamma s_k} \qquad (5)$$

in which $\gamma \cong 1.5$ for a log-compressed speckle image.

The correlation index can be described very well by an exponential decay function in inter-slice spacing d as follows:

$$CI = \exp(-d/D_z) \qquad (6)$$

where $D_z$ is the decorrelation length which is a characteristic of the elevational beam profile of the probe. Since the elevational beam profile varies with depth due to diffraction and tissue attenuation effects, $D_z$ is generally a function of depth z for a given transmit frequency. Since the beam profile is generally less coherent and complex in the near field, $D_z$ is expected to be smaller in the near-field than in the mid- and far-fields.

Given a correlation index estimate, the corresponding inter-slice spacing can be computed as follows:

$$d = -D_z \ln(CI) \qquad (7)$$

The fact that CI decays exponentially with d may prove to be an advantage for three-dimensional scanning: CI is very sensitive to small displacements or slow motion. As d increases beyond the elevational slice thickness, CI tapers off slowly towards zero. From Eq. (7), for CI<20%, a small variation in CI can translate into a large change in d. Hence, a reasonable reliability threshold (step 46 in FIG. 5) for rejecting bad correlation index samples is CI=20%, for example; that is, any value below the threshold may be caused by hand jitter or skidding of the probe. Equation (7) can be used to compute the average inter-slice spacing for the N frames based on the average value of all correlation index values greater than the reliability threshold.

Rather than use a processor to compute the average inter-slice spacing d during scanning, the relationship between d and CI can be specified by other means, such as a look-up table. However, the exponential model of Eq. (6) offers the convenience that at each depth, the relationship is completely specified by a decorrelation length. For a given probe, the decorrelation lengths for different depths or z-intervals can be calibrated by performing a controlled experiment wherein a motor-driven probe-holder is used to translate the probe at constant speed over a homogeneous scattering phantom.

In the derivation of CI, no frame averaging was assumed. In practice, frame averaging tends to produce additional correlation between adjacent acoustic frames no matter how far apart they are spaced. This means that frame averaging will cause the correlation index to decay more slowly with increasing d (larger effective $D_z$) and towards some non-zero baseline level depending on the degree of frame averaging. This has been confirmed in experimental studies which showed that the exponential decay model of Eq. (6) still holds as long as a larger effective $D_z$ is used and the reliability threshold for the correlation index is chosen above the non-zero baseline correlation associated with frame averaging effects.

The present invention is directed to a method and apparatus for calculating the inter-slice spacing and registering the slices before three-dimensional reconstruction. One preferred embodiment comprises an algorithm for registering adjacent slices by correcting for probe shift in the X and Y plane and, optionally, probe rotation about the Z axis while the probe is being translated in the Z direction during image acquisition. Another preferred embodiment corrects for probe shift in the X and Y plane and probe rotation about the X, Y and Z axes.

Figure 8:
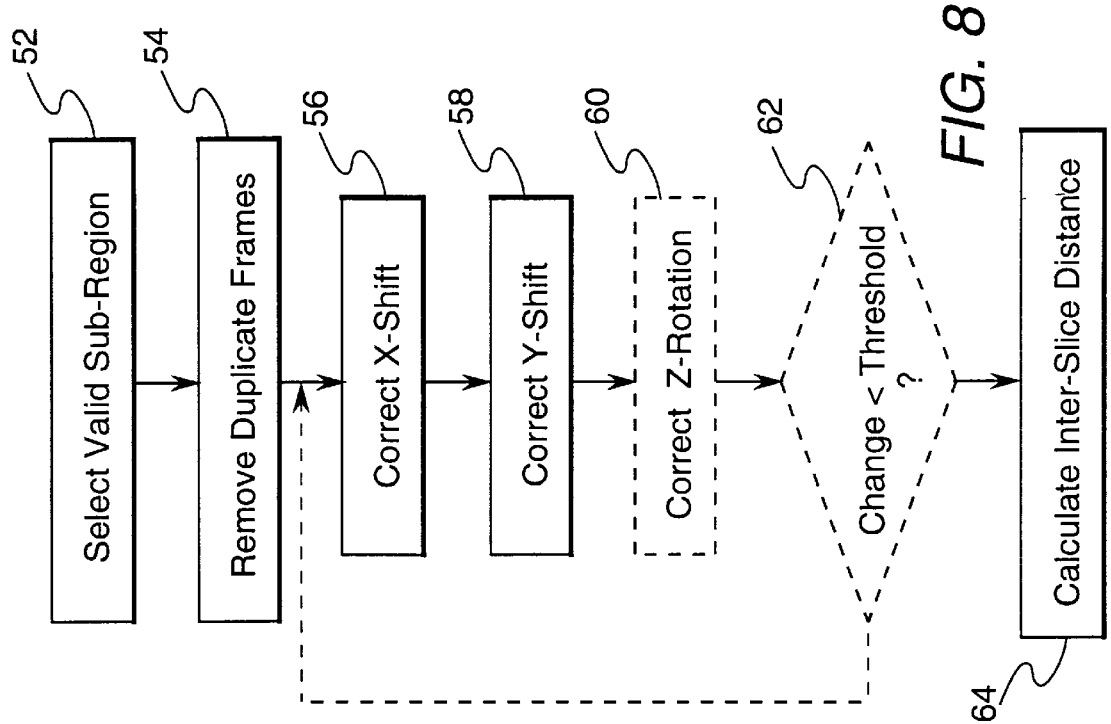
FIG. 8 is a flowchart showing the steps of an algorithm for calculating the inter-slice distance in accordance with one preferred embodiment of the invention, with optional steps indicated by dashed lines.

The method in accordance with a first preferred embodiment of the invention (shown in FIG. 8) involves a search for a minimum in the SAD of the pixel data of adjacent image frames, i.e., slices. Referring to FIG. 8, the first step in the search for a minimum SAD is to select a valid sub-region or kernel (step 52). A valid sub-region is defined as one with no back-ground pixels and pure speckle. Then duplicate frames are removed (step 54). For each pair of adjacent slices (i.e., the i-th and (i−1)-th slices), an iterative search is performed over X to determine the shift in X which produces the minimum SAD as X is varied (step 56). Similarly, an iterative search is performed over Y to determine the shift in Y which produces the minimum SAD as Y is varied (step 58). The X and Y shifts determined by these searches are then used to arrive at a final correction by which the i-th slice is registered with the (i−1)-th slice. Preferably, a so-called "exhaustive" search over X and Y can be performed, as will be discussed in detail later with reference to FIG. 11. Optionally, an iterative search is also performed to determine the angular shift about the Z axis which produces a minimum SAD (step 62). This step is not necessary if the rotation of the ultrasound probe the Z axis was insignificant. In accordance with a further option, the iterations over X and Y can be performed until the change in the SAD minima determined for successive iterations is less than a predetermined threshold. In the latter option, after each iteration the algorithm would determine whether the change in the SAD minimum as compared to the SAD minimum for the previous iteration is less than the threshold. If not, the next iteration would be carried out. If the change in the SAD minimum is less than the threshold, then the inter-slice distance would be calculated (step 64) using the technique previously disclosed and shown in FIG. 5.

Slices are typically stored in cine memory at video frame rates (typically 30 frames/sec). However, the acoustic firing rate may be much lower (perhaps 10 firings/sec). Because of this, duplicate frames may be stored in cine memory. If these frames are used in forming a three-dimensional image, the image will be distorted. In accordance with the SAD technique employed in the preferred embodiment of the invention, adjacent slices are compared by summing the absolute value of the difference between pixels in a sub-region of interest. The lower the value of SAD, the closer the two images are to being identical. If the two images are identical and no frame averaging is applied, SAD=0. If two slices have a SAD value below a given threshold, they are considered to be identical and the first of the two is eliminated. This process can be repeated for the entire data volume and thus duplicate frames can be eliminated.

Figure 9:
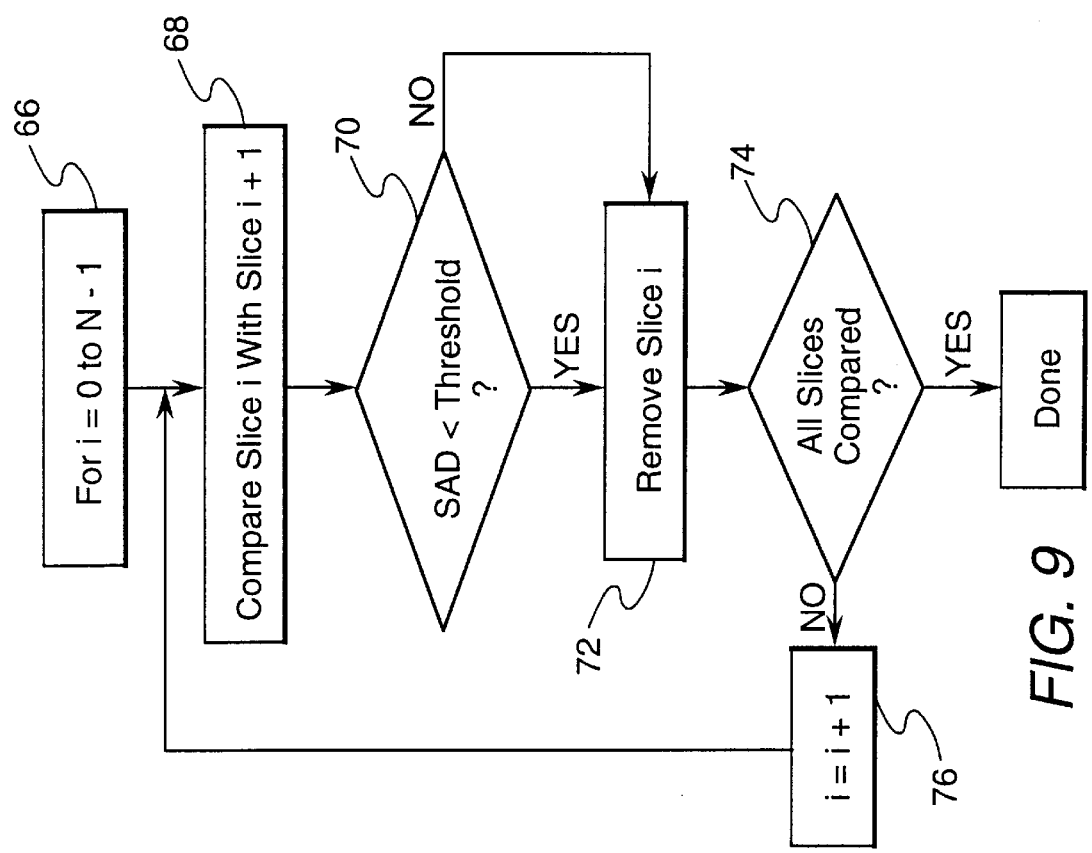
FIG. 9 is a flowchart showing the steps of an algorithm for removing duplicate frames in accordance with the preferred embodiments of the invention.

The details of the duplicate frame removal are depicted in FIG. 9. The following discussion assumes that the region of interest retrieved by the host computer from cine memory consists of N slices numbered from i=0 to i=(N−1). The algorithm depicted in FIG. 9 is performed iteratively for slices i=0 to i=(N−1) (step 66). For each iteration, the algorithm compares the i-th slice with the (i−1)-th slice by calculating the SAD of the respective pixel values (step 68). If SAD is less than a predetermined threshold (step 70), then the i-th slice will be deleted. If SAD is not less than the predetermined threshold, then the i-th slice will not be deleted. If the slices compared in the latest iteration were not slices (N−2) and (N−1), then the value of i is incremented by one (step 76) and the next iteration is performed. When all adjacent slices in the region of interest have been compared, the host computer exits the duplicate frame removal algorithm.

Figure 10:
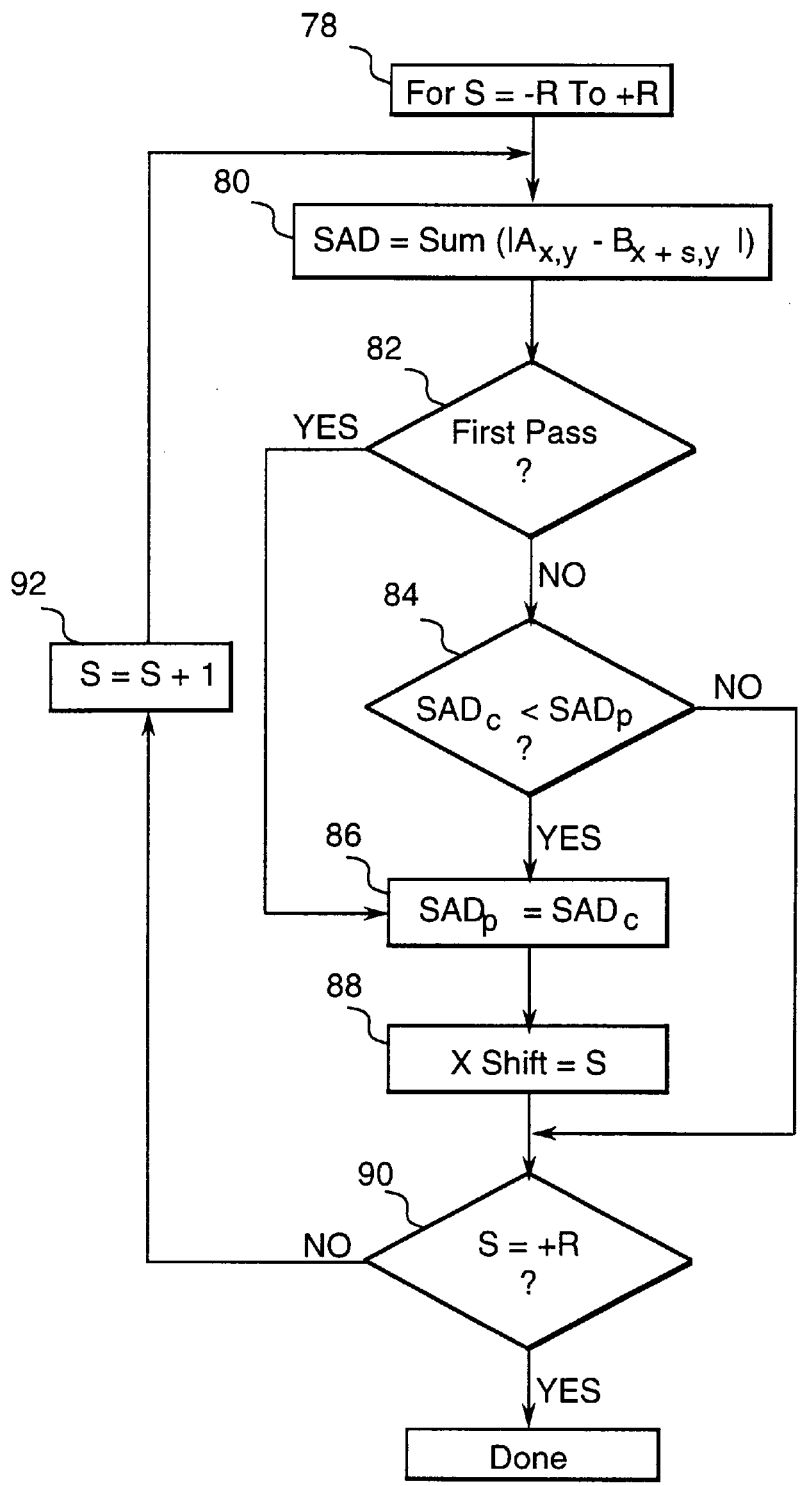
FIG. 10 is a flowchart showing the steps of an algorithm for determining the correction for relative shift in the X direction of adjacent slices of pixel data in accordance with one preferred embodiment of the invention.

FIG. 10 depicts the algorithm for determining the value needed to correct for the shift in the X direction of one slice relative to the previous slice. It should be understood that this algorithm is performed for each pair of adjacent slices in the region of interest. The variable S equals the shift in the X direction to be iteratively applied to one slice of each pair of adjacent slices in order to arrive at the minimum SAD for that pair, the shift being varied from −R to +R (step 78), where the unit of R is the pixel spacing in the X direction. For each iteration, the host computer calculates the SAD (step 80) in a kernel in accordance with the equation:

$$SAD = \sum_{x,y} |A_{x,y} - B_{x+s,y}| \qquad (8)$$

where A and B respectively denote the pixel values for the respective kernels of the i-th and (i+1)-th slices. The next step 82 determines whether the iteration being performed is the first, e.g., was S=−R. For the first iteration, the current SAD value, designated $SAD_c$, is set equal to the minimum SAD (step 86), designated $SAD_p$. The host computer sets the corrective X shift equal to the value of S for the current iteration (step 88) and then determines whether S=+R (step 90). Since S=−R for the first iteration, the host computer proceeds to the next iteration by incrementing S by one (step 92). Steps 80 and 82 are repeated for each subsequent iteration. For each iteration, the host computer determines whether SAD is less than the stored minimum SAD value, $SAD_p$ (step 84). If $SAD_c \nless SAD_p$, then the host computer repeats step 90. If S for the current iteration is not equal to +R, then S is again incremented (step 92) and the next iteration is performed. Returning to step 84, if $SAD_c < SAD_p$, then the $SAD_c$ value for the current iteration is stored as the new minimum SAD value, i.e., $SAD_p \nless SAD_c$ (step 86). The host computer then again sets the X shift equal to the value of S for the current iteration (step 88) and determines whether S=+R (step 90). The foregoing iterative process is repeated until S=+R, in response to which the host computer will exit the algorithm shown in FIG. 10. The final value for the corrective X shift will be that value of S which produced the final minimum SAD value, $SAD_p$.

For the sake of economy, the flowchart for determining the corrective Y shift for each pair of adjacent slices is not shown in the drawings. The person skilled in the art will readily appreciate that such a flowchart would be similar to that shown in FIG. 10, except that instead Eq. (8), the following equation would be used in step 80:

$$SAD = \sum_{x,y} |A_{x,y} - B_{x,y+s}| \tag{9}$$

Figure 11:
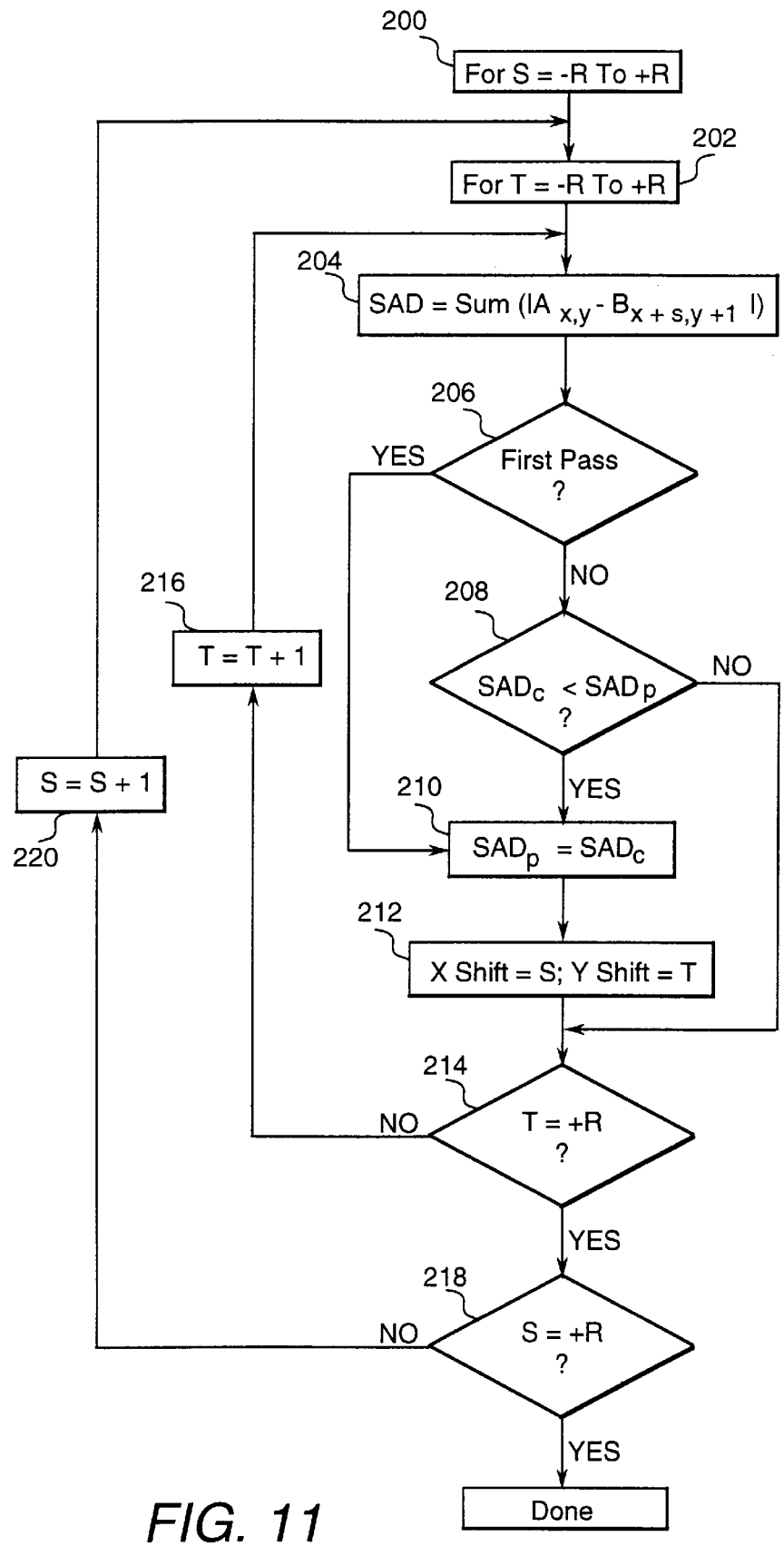
FIG. 11 is a flowchart showing the steps of an algorithm for determining the corrections for relative shifts in both the X and Y directions of adjacent slices of pixel data in accordance with another preferred embodiment of the invention.

In accordance with the preferred embodiment of the invention, the corrective X and Y shifts in a so-called "exhaustive" search shown in FIG. 11. In this case, the variables S and T respectively equal the shifts in the X and Y directions to be iteratively applied to one slice of each pair of adjacent slices in order to arrive at the minimum SAD for respective kernels of that pair, the shift S being varied from −R to +R (step 200) and the shift T being varied from −R to +R for each S (step 202), where R is the pixel spacing (assumed to be the same in the X and Y directions). For each iteration, the host computer calculates the SAD (step 204) in accordance with the equation:

$$SAD = \sum_{x,y} |A_{x,y} - B_{x+s,y+t}| \tag{10}$$

where again A and B respectively denote the pixel values for respective kernels of the i-th and (i−1)-th slices. The next step 206 determines whether the iteration being performed is the first. For the first iteration, the current SAD value, designated $SAD_c$, is set equal to the minimum SAD (step 210), designated $SAD_p$. The host computer sets the corrective X shift equal to the value of S and the corrective Y shift equal to the value of T for the current iteration (step 212) and then determines whether T=+R (step 214). Since T=−R for the first iteration, the host computer proceeds to the next iteration by incrementing T by one (step 92). Steps 204 and 206 are repeated for each subsequent iteration as T is incremented from −R to +R. For each iteration, the host computer determines whether $SAD_c$ is less than the stored minimum SAD value, $SAD_p$ (step 208). If $SAD_c \nless SAD_p$, then the host computer repeats step 214. If $SAD_c < SAD_p$, then the $SAD_c$ value for the current iteration is stored as the new minimum SAD value, i.e., $SAD_p \nless SAD_c$ (step 210). The host computer then again sets the corrective X shift equal to the value of S and the corrective Y shift equal to the value of T for the current iteration (step 212) and then determines whether T=+R (step 214). If T=+R, the host computer then determines if S=+R (step 218). If S≠+R, then S is incremented by one (step 220) and then a further round of iterations are performed for T=−R to T=+R, each iteration determining whether the current SAD is less than the current minimum SAD and substituting the former for the latter if it is less. The corresponding corrective X and Y shifts are stored. This process is in turn repeated for S=−R to S=+R. When S=+R, the final corrective X and Y shifts corresponding to the minimum SAD will be used in the subsequent registration of the two slices being processed. The algorithm shown in FIG. 11 is performed for each pair of adjacent slices in the region of interest.

Figure 12:
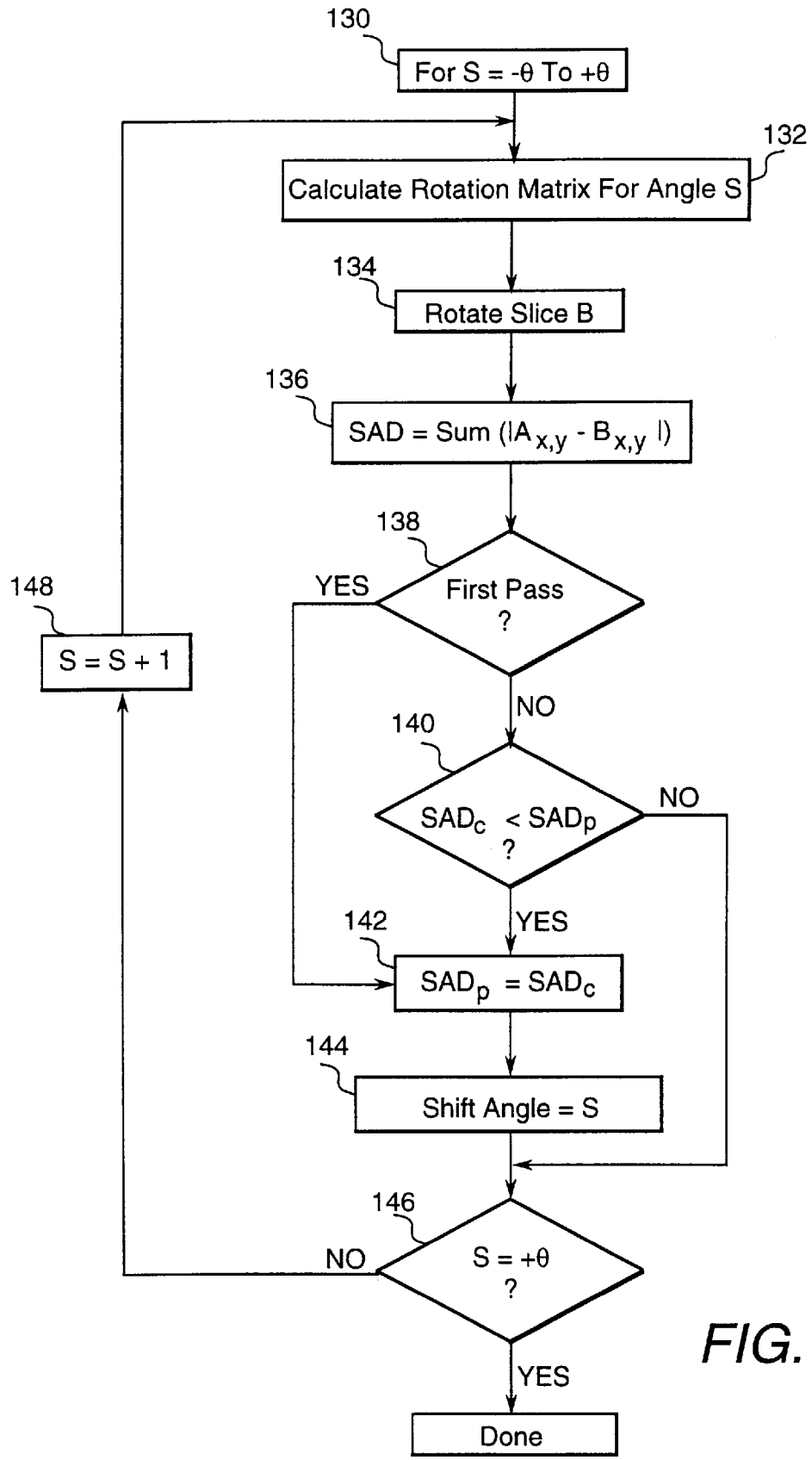
FIG. 12 is a flowchart showing the steps of an algorithm for determining the correction for relative rotation about the Z axis of adjacent slices of pixel data in accordance with another preferred embodiment of the invention.

The optional correction for rotation about the Z axis is performed using the algorithm depicted in FIG. 12. It should be understood that this algorithm is performed for each pair of adjacent slices in the region of interest. The variable S in FIG. 12 represents the angular shift about the Z axis to be iteratively applied to one slice relative to the other slice in order to arrive at the minimum SAD for that pair of adjacent slices, the angular shift being varied from −θ to +θ (step 78), where the unit of θ is angular degree. For each angular shift S, the host computer calculates a rotation matrix (step 132). That rotation matrix is then used to rotate slice B relative to slice A (step 134). The host computer then calculates the SAD for each S (step 136) in accordance with the equation:

$$SAD = \sum_{x,y} |A_{x,y} - B_{x,y}| \tag{11}$$

where A and B respectively denote the pixel values for the respective kernels of the i-th and (i+1)-th slices. The next step 138 determines whether the iteration being performed is the first, e.g., was S=−θ. For the first iteration, the current SAD value, $SAD_c$, is set equal to the minimum SAD (step 142), $SAD_p$. The host computer sets the corrective shift angle equal to the value of S for the current iteration (step 144) and then determines whether S=+θ (step 146). Since S=−θ for the first iteration, the host computer proceeds to the next iteration by incrementing S by one (step 148). Steps 132, 134, 136 and 138 are repeated for each subsequent iteration. For each iteration, the host computer determines whether $SAD_c$ is less than the stored minimum SAD value, $SAD_p$ (step 140). If $SAD_c \nless SAD_p$, then the host computer repeats step 146. If S for the current iteration is not equal to +R, then S is incremented (step 148) and the next iteration is performed. Returning to step 140, if $SAD_c < SAD_p$, then the $SAD_c$ value for the current iteration is stored as the new minimum SAD value, i.e., $SAD_p \nless SAD_c$ (step 142). The host computer then again sets the angular shift equal to the value of S for the current iteration (step 144) and determines whether S=+θ (step 146). The foregoing iterative process is repeated until S=+θ, in response to which the host computer will exit the algorithm shown in FIG. 12. The final value for the corrective angular shift will be that value of S which produced the final minimum SAD value, $SAD_p$.

In accordance with one preferred embodiment of the invention, the corrective translational and rotational shifts determined using the algorithms of FIGS. 11 and 12 are employed in the algorithm depicted in FIG. 8.

Figure 13:
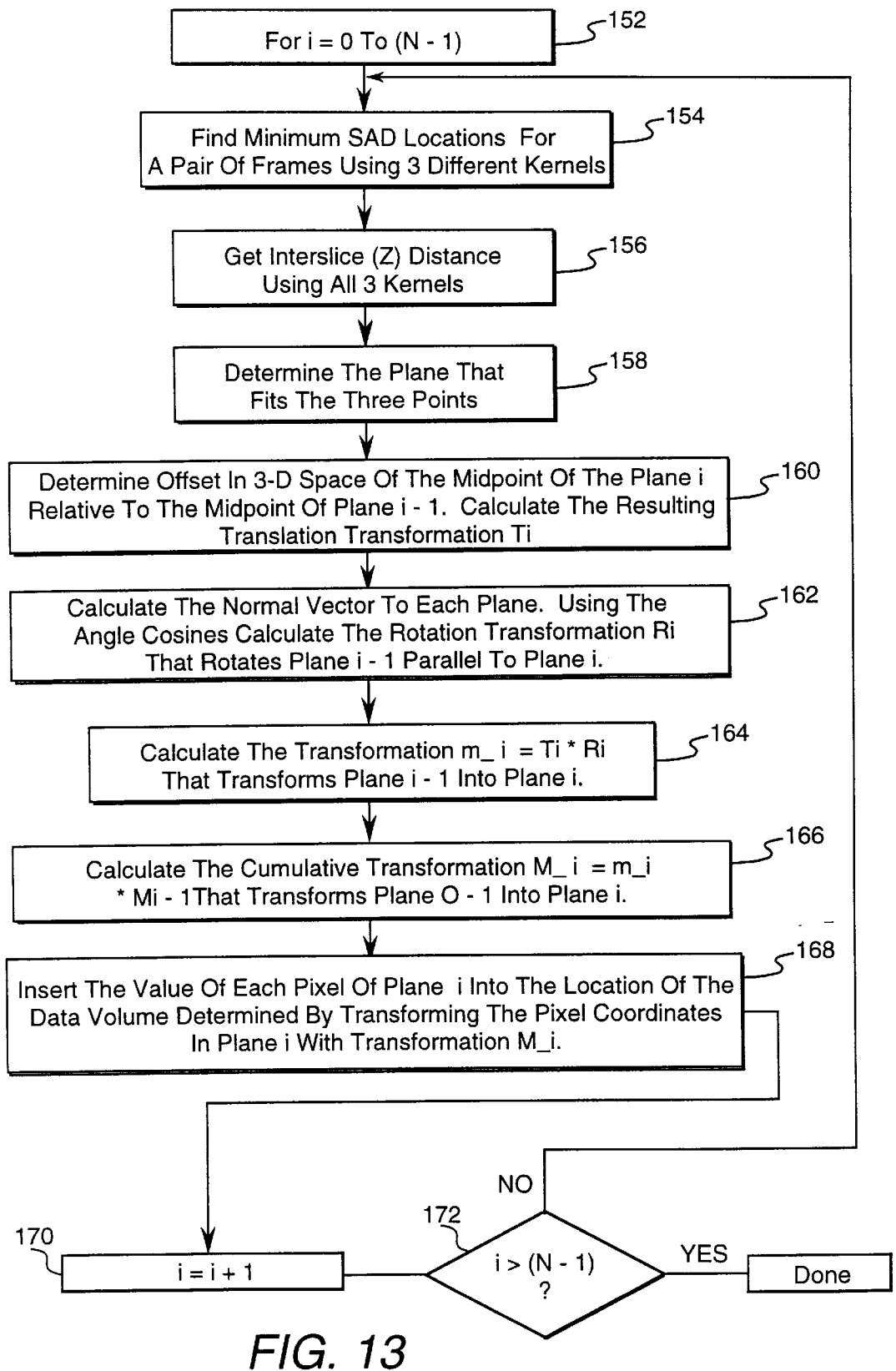
FIG. 13 is a flowchart showing the steps of an algorithm for re-registering the slices of a pixel data volume in accordance with yet another preferred embodiment of the invention.

The method in accordance with an alternative preferred embodiment is depicted in FIG. 13. The host computer performs the iteration process shown in FIG. 13 for each of slices 0 through (N−1) (block 152). For each pair of adjacent frames being processed, the host computer finds minimum SAD locations using three different kernels (step 154) and then calculates the inter-slice spacing of the two slices for each kernel (step 156), using the technique of FIG. 5. Each inter-slice spacing determines a respective point, which is used to determine the equation of a plane i which fits, i.e., intersects, the determined points (step 158). Based on the equation for plane i, the host computer calculates the pixel coordinates of the midpoint of plane i and the inter-slice spacing separating that midpoint from the midpoint of plane (i−1). The host computer then determines the offset in three-dimensional space of the respective midpoints of planes i and (i−1), and calculates a translation transformation $T_i$ which places those midpoints in registration (step 160), i.e., which eliminates the offset between the midpoints. Then the host computer calculates the normal vector to each plane and, using the angle cosines, calculates a rotation transformation $R_i$ which renders those normal vectors mutually parallel (step 162), i.e., which rotates plane (i−1) parallel to plane i. The translation and rotation transformations are then used to calculate (step 164) a transformation $m_i$ that transforms plane (i−1) into plane i in accordance with the equation:

$$m_i = T_i \times R_i$$

This is done for each plane in order to calculate (step 166) a cumulative transformation $M_i$ that transforms plane 0 into plane i:

$$M_i = m_i \times M_{i-1}$$

The pixel values of plane i are then inserted into the location in the data volume determined by transforming the pixel coordinates in plane i with the cumulative transformation $M_i$ (step 168). This algorithm is repeated for each iteration (step 170) until all slices 0 through (N−1) have been processed (step 172). The resulting transformed data volume, with determined inter-slice spacings, can then be processed in accordance with a three-dimensional projection technique.

While the invention has been described with reference to a preferred embodiment, it will be understood by those skilled in the art that various changes may be made and equivalents may be substituted for elements thereof without departing from the scope of the invention. In addition, many modifications may be made to adapt a particular situation to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims.

What is claimed is:

1. An imaging system comprising:

a transducer array comprising a multiplicity of transducer elements for transmitting wave energy in response to electrical activation and transducing returned wave energy into electrical signals;

a transmitter coupled to said transducer array and programmed to activate a plurality of said transducer elements to transmit focused wave energy for each of a multiplicity of transmit focal positions in each of a multiplicity of scan planes;

a receiver programmed to form receive signals from electrical signals output from said plurality of transducer elements subsequent to each transmit for each of a multiplicity of scan lines in each scan plane;

a processing subsystem for converting said receive signals into pixel data for each scan line in each scan plane;

memory for storing a respective slice of pixel data for each scan plane to form a data volume;

means for registering slices of said data volume using sum of the absolute differences (SAD) calculations for the pixel values in respective kernels of adjacent slices;

means for projecting the pixel values of said registered slices to form projected image data; and a subsystem for displaying a projected image which is a function of said projected image data.

2. The system as recited in claim 1, further comprising means for calculating respective inter-slice spacings separating adjacent slices of said data volume using SAD calculations for the pixel values in respective kernels of adjacent slices.

3. The system as recited in claim 1, further comprising means for discarding substantially duplicate slices using SAD calculations for the pixel values in respective kernels of adjacent slices, said duplicate slice discarding being performed before registration and before calculation of inter-slice spacings.

4. The system as recited in claim 1, wherein said registering means comprise means for determining a translational shift in a coordinate direction of a second slice relative to a first slice corresponding to an SAD calculation for the pixel values in respective kernels of said first and second slices within a predetermined threshold of a minimum.

5. The system as recited in claim 1, wherein said registering means comprise means for determining a rotational shift about a coordinate axis of a second slice relative to a first slice corresponding to an SAD calculation for the pixel values in respective kernels of said first and second slices within a predetermined threshold of a minimum.

6. The system as recited in claim 1, wherein said registering means comprise:

means for finding minimum SAD locations using at least three different kernels for first and second slices in said data volume;

means for calculating the inter-slice spacing of said first and second slices for each kernel based on the SAD of respective pixel values in each kernel; and the SAD of respective pixel values in each kernel; and means for determining a plane i as a function of said inter-slice spacings at respective points in said second slice and a plane (i−1) as a function of said first slice.

7. The system as recited in claim 6, further comprising means (20) for calculating an inter-slice spacing separating corresponding points of planes i and (i−1).

8. The system as recited in claim 6, wherein said registering means further comprise:

means for calculating a transformation that transforms plane (i−1) into plane i; and means for inserting the pixel values of plane i into the location in the data volume determined by transforming the pixel coordinates in plane i with said transformation.

9. The system as recited in claim 8, wherein said transformation calculating means comprise:

means for determining an offset of a point of plane i relative to a point of plane (i−1);

means for calculating a translation transformation which eliminates said offset between said points of planes i and (i−1);

means for calculating the normal vector to each of planes i and (i−1); and means for calculating a rotation transformation which rotates plane (i−1) parallel to plane i.

10. A system for three-dimensional imaging of an object volume, comprising:
an ultrasound transducer array for transmitting ultrasound beams and detecting ultrasound echoes reflected from said object volume at a multiplicity of sample volumes in a scan plane;
a display monitor; and
a computer programmed to perform the following steps:
(a) activating transducer elements of said array to transmit focused wave energy for each of a multiplicity of transmit focal positions in each of a multiplicity of scan planes;
(b) forming receive signals from electrical signals output from said plurality of transducer elements subsequent to each transmit for each of a multiplicity of scan lines in each scan plane;
(c) converting said receive signals into pixel data for each scan line in each scan plane;
(d) storing a respective slice of pixel data for each scan plane to form a data volume;
(e) registering slices of said data volume using sum of the absolute differences (SAD) calculations for the pixel values in respective kernels of adjacent slices;
(f) projecting the pixel values of said registered slices to form projected image data; and
(g) controlling said display monitor to display a projected image which is a function of said projected image data.

11. The system as recited in claim 10, wherein said computer is further programmed to calculate respective inter-slice spacings separating adjacent slices of said data volume using SAD calculations for the pixel values in respective kernels of adjacent slices.

12. The system as recited in claim 10, wherein said computer is further programmed to discard substantially duplicate slices using SAD calculations for the pixel values in respective kernels of adjacent slices, said duplicate slice discarding being performed before registration and before calculation of inter-slice spacings.

13. The system as recited in claim 10, wherein said registering step comprises the step of determining a translational shift in a coordinate direction of a second slice relative to a first slice corresponding to an SAD calculation for the pixel values in respective kernels of said first and second slices within a predetermined threshold of a minimum.

14. The system as recited in claim 10, wherein said registering step comprises the step of determining a rotational shift about a coordinate axis of a second slice relative to a first slice corresponding to an SAD calculation for the pixel values in respective kernels of said first and second slices within a predetermined threshold of a minimum.

15. The system as recited in claim 10, wherein said registering step comprises the following steps:
finding minimum SAD locations using at least three different kernels for first and second slices in said data volume;
calculating the inter-slice spacing of said first and second slices for each kernel based on the SAD of respective pixel values in each kernel; and
determining a plane i as a function of said inter-slice spacings at respective points in said second slice and a plane (i−1) as a function of said first slice.

16. The system as recited in claim 15, wherein said computer is further programmed to calculate an inter-slice spacing separating corresponding points of planes i and (i−1).

17. The system as recited in claim 15, wherein said registering step further comprises the following steps:
calculating a transformation that transforms plane (i−1) into plane i; and
inserting the pixel values of plane i into the location in the data volume determined by transforming the pixel coordinates in plane i with said transformation.

18. The system as recited in claim 17, wherein said transformation calculating step comprises:
determining an offset of a point of plane i relative to a point of plane (i−1);
calculating a translation transformation which eliminates said offset between said points of planes i and (i−1);
calculating the normal vector to each of planes i and (i−1); and
calculating a rotation transformation which rotates plane (i−1) parallel to plane i.

19. A method for three-dimensional imaging of a volume of matter, comprising the steps of:
transmitting focused wave energy for each of a multiplicity of transmit focal positions in each of a multiplicity of scan planes intersecting the volume of matter;
generating echo signals derived from echoes of wave energy returned from the volume of matter following each transmit for each of a multiplicity of scan lines in each scan plane;
converting said receive signals into pixel data for each scan line in each scan plane;
storing a respective slice of pixel data for each scan plane to form a data volume;
registering slices of said data volume using SAD calculations for the pixel values in respective kernels of adjacent slices;
projecting the pixel values of said registered slices to form projected image data; and
displaying a three-dimensional image which is a function of said projected image data.

20. The method as recited in claim 19, further comprising the step of calculating respective inter-slice spacings separating adjacent slices of said data volume using SAD calculations for the pixel values in respective kernels of adjacent slices.

21. The method as recited in claim 19, further comprising the step of discarding substantially duplicate slices using SAD calculations for the pixel values in respective kernels of adjacent slices, said duplicate slice discarding being performed before registration and before calculation of inter-slice spacings.

22. The method as recited in claim 19, wherein said registering step comprises the step of determining a translational shift in a coordinate direction of a second slice relative to a first slice corresponding to an SAD calculation for the pixel values in respective kernels of said first and second slices within a predetermined threshold of a minimum.

23. The method as recited in claim 19, wherein said registering step comprises the step of determining a rotational shift about a coordinate axis of a second slice relative to a first slice corresponding to an SAD calculation for the pixel values in respective kernels of said first and second slices within a predetermined threshold of a minimum.

24. The method as recited in claim 19, wherein said registering step comprises the following steps:
finding minimum SAD locations using at least three different kernels for first and second slices in said data volume;

calculating the inter-slice spacing of said first and second slices for each kernel based on the SAD of respective pixel values in each kernel; and determining a plane i as a function of said inter-slice spacings at respective points in said second slice and a plane (i−1) as a function of said first slice.

25. The method as recited in claim 24, wherein said computer is further programmed to calculate an inter-slice spacing separating corresponding points of planes i and (i−1).

26. The method as recited in claim 24, wherein said registering step further comprises the following steps:

calculating a transformation that transforms plane (i−1) into plane i; and inserting the pixel values of plane i into the location in the data volume determined by transforming the pixel coordinates in plane i with said transformation.

27. A method for registering image frames of pixel data, comprising the steps of:

finding minimum SAD locations using at least three different kernels for first and second image frames of pixel data;

calculating the spacing of said first and second image frames for each kernel based on the SAD of respective pixel values in each kernel;

determining a first plane as a function of said spacing at respective points in said image frame and relative to a second plane corresponding to said first image frame;

calculating a transformation that transforms said first plane into said second plane; and inserting the pixel values of said first plane into locations determined by transforming the pixel coordinates in said first plane with said transformation.

28. A method for calculating a spacing between image frames of pixel data, comprising the steps of:

finding minimum SAD locations using at least three different kernels for first and second image frames of pixel data;

calculating the spacing of said first and second image frames for each kernel based on the SAD of respective pixel values in each kernel;

determining a first plane as a function of said spacing at respective points in said image frame and relative to a second plane corresponding to said first image frame; and calculating an inter-slice spacing separating corresponding points of said first and second planes.

29. A system for registering image frames of pixel data, comprising:

memory storing first and second image frames of pixel data; and a computer programmed to perform the following steps:

(a) finding minimum SAD locations using at least three different kernels for said first and second image frames of pixel data;

(b) calculating the spacing of said first and second image frames for each kernel based on the SAD of respective pixel values in each kernel;

(c) determining a first plane as a function of said spacing at respective points in said image frame and relative to a second plane corresponding to said first image frame;

(d) calculating a transformation that transforms said first plane into said second plane; and (e) inserting the pixel values of said first plane into locations determined by transforming the pixel coordinates in said first plane with said transformation.

30. A system for calculating a spacing between image frames of pixel data, comprising:

memory storing first and second image frames of pixel data; and a computer programmed to perform the following steps:

(a) finding minimum SAD locations using at least three different kernels for said first and second image frames of pixel data;

(b) calculating the spacing of said first and second image frames for each kernel based on the SAD of respective pixel values in each kernel;

(c) determining a first plane as a function of said spacing at respective points in said image frame and relative to a second plane corresponding to said first image frame; and (d) calculating an inter-slice spacing separating corresponding points of said first and second planes.

* * * * *